United States Patent [19]

Molina et al.

[11] Patent Number: 5,900,431
[45] Date of Patent: May 4, 1999

[54] USE OF FUMAGILLOL AND DERIVATIVES THEREOF FOR PREPARING MEDICAMENTS AGAINST INTESTINAL INFECTIONS

[75] Inventors: Jean-Michel Molina, Paris; Francis Derouin, Saint Germain En Laye, both of France

[73] Assignee: Sanofi, Paris, France

[21] Appl. No.: 08/913,360

[22] PCT Filed: Mar. 26, 1996

[86] PCT No.: PCT/FR96/00448

§ 371 Date: Sep. 17, 1997

§ 102(e) Date: Sep. 17, 1997

[87] PCT Pub. No.: WO96/30010

PCT Pub. Date: Oct. 3, 1996

[30] Foreign Application Priority Data

Mar. 27, 1995 [FR] France ................... 95 03549

[51] Int. Cl.⁶ ............... A61K 9/20; A61K 9/22; A61K 9/48; A61K 9/52
[52] U.S. Cl. ............ 514/475; 424/451; 424/457; 424/464; 424/468
[58] Field of Search ................................. 514/475

[56] References Cited

U.S. PATENT DOCUMENTS

| 2,791,530 | 5/1957 | Dallavis et al. | 167/65 |
| 5,328,930 | 7/1994 | Wilson | 514/475 |

FOREIGN PATENT DOCUMENTS

| 2002814 | 5/1996 | Canada . |
| 799 616 | 10/1997 | European Pat. Off. . |
| 819430 | 1/1998 | European Pat. Off. . |
| 62-000476 A2 | 1/1987 | Japan . |
| 92 02240 | 2/1992 | WIPO . |
| 963 00 10 | 10/1996 | WIPO . |
| 98 05293 | 2/1998 | WIPO . |

OTHER PUBLICATIONS

Molina et al AIDS (London) 11(13):1603–1610, 1997.

*Primary Examiner*—Shep K. Rose
*Attorney, Agent, or Firm*—Bacon & Thomas

[57] ABSTRACT

The invention relates to the use of fumagillol and the esters formed by fumagillol and saturated or unsaturated ($C_1$–$C_{12}$) alkylcarboxylic or ($C_1$–$C_{12}$) alkyldicarboxylic acids, and their pharmaceutically acceptable salts, for the preparation of medicaments for combating intestinal infections caused by microsporidia and/or cryptosporidia.

12 Claims, No Drawings

USE OF FUMAGILLOL AND DERIVATIVES THEREOF FOR PREPARING MEDICAMENTS AGAINST INTESTINAL INFECTIONS

The present invention relates to a novel use of fumagillol and its derivatives, especially fimagillin.

Fumagillin is an antibiotic, first described in 1951 (The Merck Index 11th Edition, no. 4199), which is used especially for preventing or controlling parasitic diseases in fish farming and beekeeping and which has also been used in man for the local treatment, in an eye lotion, of keratoconjunctivitis due to *Encephalitozoon hellem* (J. Ophtal., 1993, 115, 293). However, it has been found to be inactive as a carcinolytic agent (Antibiotic Annual, 1958–1959, 541–546).

It has now been found that fumagillol and certain esters formed with this compound, when formulated in a drug, especially an oral drug, are capable of resolving very serious infectious conditions of the intestine due to microsporidia or cryptosporidia.

It has also been found, surprisingly, that fuimagillol and the esters formed by fumagillol and saturated or unsaturated ($C_1$–$C_{12}$) alkylcarboxylic or ($C_1$–$C_{12}$) alkyldicarboxylic acids are capable of inducing eradication of *Enterocytozoon bieneusi* in patients affected by HIV. This discovery is surprising and decisive because there is currently no known remedy for this type of infection, which constitutes 95% of the intestinal infections due to microsporidia which result in cachexia and death in patients suffering from AIDS.

Thus, according to one of its features, the present invention relates to the use of fumagillol or esters formed by fuimagillol and saturated or unsaturated ($C_1$–$C_{12}$) alkylcarboxylic or ($C_1$–$C_{12}$) alkyldicarboxylic acids, and their pharmaceutically acceptable salts, for the preparation of drugs for combating intestinal infections due to microsporidia and/or cryptosporidia.

More particularly and advantageously, according to its preferred feature, the present invention relates to the use of fumagillol or esters formed by fumagillol and saturated or unsaturated ($C_1$–$C_{12}$) alkylcarboxylic or ($C_1$–$C_{12}$) alkyldicarboxylic acids, and their pharmaceutically acceptable salts, for the preparation of drugs for combating intestinal infections for which the parasite *Enterocytozoon bieneusi* is principally responsible.

"Saturated or unsaturated ($C_1$–$C_{12}$) alkylcarboxylic or ($C_1$–$C_{12}$) alkyldicarboxylic acids" are understood as meaning carboxylic or dicarboxylic acids of linear or branched alkyls, it being possible for said alkyls to contain one or more double bonds.

Examples of such acids are acetic, propionic, butyric, valeric, pivalic, malonic, succinic, acrylic, crotonic, isocrotonic, oleic, maleic, fumaric and 2,4,6,8-decatetraenedioic acids.

The ester of fumagillol and 2,4,6,8-decatetraenedioic acid, fumagillin, is a particularly advantageous compound.

The esters of the present invention are easily prepared by reacting fumagillol with the appropriate acid under the normal esterification conditions described in the literature.

Fumagillol, either as such or esterified with a ($C_1$–$C_{12}$) alkylcarboxylic or ($C_1$–$C_{12}$) alkyldicarboxylic acid, can be administered in the form of the free acid or else in the form of one of its salts with a pharmaceutically acceptable base.

For their administration to patients suffering from an infection due to microsporidia or cryptosporidia, fumagillol or the esters formed therewith are mixed with pharmaceutical excipients commonly used for the preparation of pharmaceutical formulations, preferably for oral administration.

Advantageously, the compounds of the present invention are formulated as active principles in dosage units, for example tablets or gelatin capsules, containing from 1 to 200 mg of active principle, advantageously from 2 to 100 mg, more advantageously from 5 to 50 mg or preferably from 7.5 to 30 mg per dosage unit.

The pharmaceutical compositions for oral administration constitute a further subject of the present invention.

In the pharmaceutical compositions of the present invention for oral administration, the active principle can be administered in the above-mentioned unit forms of administration, mixed with conventional pharmaceutical carriers, for the treatment of the above-mentioned diseases. The appropriate unit forms of administration include oral forms such as tablets, which may be scored, gelatin capsules, powders, granules and solutions or suspensions to be taken orally.

When a solid composition is prepared in the form of tablets, which is one of the preferred forms, the main active ingredient is mixed with a pharmaceutical vehicle such as gelatin, starch, lactose, magnesium stearate, talcum, gum arabic or the like. The tablets can be coated with sucrose or other appropriate substances or else they can be treated so as to have a prolonged or delayed activity and so as to release a predetermined amount of active principle continuously. These delayed action or controlled release tablets represent another very advantageous form.

A preparation in the form of gelatin capsules, which is another particularly advantageous form, is obtained by mixing the active ingredient with a diluent and pouring the resulting mixture into soft or hard gelatin capsules.

A preparation in the form of a syrup or elixir can contain the active ingredient together with a sweetener, which is preferably calorie-free, methylparaben and propylparaben as antiseptics, as well as a flavoring and an appropriate color.

The water-dispersible granules or powders can contain the active ingredient mixed with dispersants or wetting agents or with suspending agents such as polyvinylpyrrolidone, as well as with sweeteners or taste correctors.

The active principle can also be formulated as microcapsules, optionally with one or more carriers or additives.

In the pharmaceutical compositions according to the present invention, the active principle can also be in the form of an inclusion complex in cyclodextrins, their ethers or their esters.

Pharmaceutical compositions for oral administration, containing from 1 to 200 mg, preferably from 2 to 100 mg, from 5 to 50 mg or from 7.5 to 30 mg, of fumagillol, an ester formed by fumagillol and one of the acids mentioned above, especially fimagillin, or one of their pharmaceutically acceptable salts as the active principle, in a form selected from tablets, delayed action tablets, controlled release tablets and gelatin capsules, constitute a further subject of the present invention.

The compounds of the present invention can be administered with other drugs generally used during the development of AIDS, and can also be formulated in association with other antiparasitics or antibiotics or with drugs having an anti-HIV action.

The therapeutic activity of the compounds of the present invention was demonstrated by administering different doses of the pharmaceutical composition of Example I to four homosexual patients of the male sex presenting a high immune deficiency with an average CD4 level of 66 (11-158). Three patients had recognized AIDS and one patient had an ARC (Aids Related Complex). The average age was 40 years.

Prior to inclusion, all these patients had consecutive stool examinations which were positive for microsporidia. Two patients concomitantly presented an intestinal infection with cryptosporidia. The test for microsporidia in the urine remained negative in all the patients, these factors favoring the diagnosis of infection with *Enterocytozoon bieneusi*.

All the patients had a duodenal fibroscopy with biopsies. In three patients, microsporidia were identified on these biopsies in histology and in direct parasitology, as well as by electron microscopy. In the fourth case, only electron microscopy revealed the presence of *Enterocytozoon bieneusi*.

The four patients received 20 mg of fumagillin three times a day, i.e. 60 mg/d, for 21 days.

Eradication of the parasite from the stool was observed in all the patients in the control examinations after 15, 17 and 21 days of treatment. Microsporidia were still absent from the patients' stool one month after cessation of the treatment.

Of the two patients who presented cryptosporidia in their stool prior to inclusion, only one transitorily tested negative on his stool, cryptosporidia reappearing one month after cessation of the treatment.

All the patients had a control duodenal fibroscopy to assess the disappearance of the parasites at tissue level. Also, in two cases, a negative result was observed in histology, with the persistence of very rare microsporidia in direct parasitology (probably cadavers of microsporidia). The electron microscopy study confirmed the total disappearance of *Enterocytozoon bieneusi* in all four patients.

Another group of patients was recruited for a tolerance/toxicology study. Doses of 10, 20, 40 and 60 mg of fumagillin were administered to twenty-four patients (six per dose level).

The treatment was tolerated well. In particular, no hepatic toxicity, cardiac toxicity (ECG) or renal toxicity (creatininemia) was observed. Even a very slight decrease in the serum alkaline phosphatase level was noted, which could correspond to a beneficial effect of the treatment on cholangitis due to microsporidia.

The troublesome side effect observed was of the hematological type, namely thrombopenia which varied in degree but was never very severe (except in one case which caused the administration to be interrupted in the above group of four patients) and whose evolution was spontaneously regressive in 10 to 14 days after cessation of the treatment. This side effect, which is not immunological but due solely to a direct toxicity towards the platelets, can be corrected by an appropriate choice of treatment protocol.

In conclusion, eradication of the parasite from the stool was observed for the first time in this opportunistic infection; this eradication persists for at least one month after cessation of the treatment and seems to be accompanied by eradication of the parasite from the duodenal biopsies. This result has never been achieved with other antiparasitics.

The clinical benefit is difficult to evaluate in these patients in view of the multiple associated infections and the pursuance of symptomatic treatments. A very marked clinical benefit was nevertheless obtained in the patients treated, who all gained several kilograms and whose diarrhea stopped at the end of the treatment.

Consequently, spectacular parasitological results were obtained with fumagillin in *Enterocytozoon bieneusi* infections in the course of AIDS, with an excellent clinical result in some cases.

EXAMPLE 1

Pharmaceutical composition in the form of gelatin capsules each containing 20 mg of fumagillin acid 14 g of purified and pre-sieved fumagillin acid are gradually diluted to a volume of 210 ml with the requisite amount of colloidal silica (AEROSIL®). The powder obtained is mixed thoroughly and the homogeneous powder prepared in this way is divided up into no. 3 opaque hard gelatin capsules. This gives 700 gelatin capsules each containing 20 mg of flimagillin acid.

We claim:

1. A method of treating intestinal infections due to microsporidia and/or cryptosporidia which comprises orally administering to a subject in need thereof an effective amount of fumagillol, an ester formed by fumagillol and a saturated or unsaturated ($C_1$–$C_{12}$) alkylcarboxylic or ($C_1$–$C_{12}$) alkyldicarboxylic acid, or a pharmaceutically acceptable salt thereof.

2. A method according to claim 1 wherein said ester is fumagillin.

3. A method according to claim 1 for treating intestinal infections for which the parasite *Enterocytozoon bieneusi* is principally responsible.

4. A method according to claim 3 wherein said ester is fumagillin.

5. A method according to claim 1 wherein oral administration is effected by means of tablets, gelatin capsules or delayed action or controlled release tablets.

6. A method according to claim 2 wherein oral administration is effected by means of tablets, gelatin capsules or delayed action or controlled release tablets.

7. A method according to claim 3 wherein oral administration is effected by means of tablets, gelatin capsules or delayed action or controlled release tablets.

8. A method according to claim 4 wherein oral administration is effected by means of tablets, gelatin capsules or delayed action or controlled release tablets.

9. A method according to claim 5, wherein said effective amount is in the range 1–200 mg.

10. A method according to claim 6, wherein said effective amount is in the range 1–200 mg.

11. A method according to claim 7, wherein said effective amount is in the range 1–200 mg.

12. A method according to claim 8, wherein said effective amount is in the range 1–200 mg.

* * * * *